(12) United States Patent
Kweon et al.

(10) Patent No.: US 12,324,867 B2
(45) Date of Patent: Jun. 10, 2025

(54) HYALURONATE FIBER AND MANUFACTURING METHOD THEREOF

(71) Applicant: JINWOO BIO CO., LTD., Seoul (KR)

(72) Inventors: Dong Keon Kweon, Yongin-si (KR); Sin Hwan Kwon, Seoul (KR); Jong Soo Kim, Bucheon-si (KR); Da Wei Li, Seoul (KR); Myoung Han Lee, Seoul (KR); Hyun Ho Lee, Incheon (KR); Young Chan Jeon, Incheon (KR); Joo Yeon Hong, Guri-si (KR)

(73) Assignee: JINWOO BIO CO., LTD., Seoul (KR)

( * ) Notice: Subject to any disclaimer, the term of this patent is extended or adjusted under 35 U.S.C. 154(b) by 1051 days.

(21) Appl. No.: 17/254,057

(22) PCT Filed: Nov. 27, 2020

(86) PCT No.: PCT/KR2020/017059
§ 371 (c)(1),
(2) Date: Dec. 18, 2020

(87) PCT Pub. No.: WO2022/114286
PCT Pub. Date: Jun. 2, 2022

(65) Prior Publication Data
US 2022/0160932 A1    May 26, 2022

(30) Foreign Application Priority Data
Nov. 26, 2020  (KR) .......................... 10-2020-0161390

(51) Int. Cl.
| | |
|---|---|
| A61L 27/20 | (2006.01) |
| A61L 17/00 | (2006.01) |
| A61L 27/54 | (2006.01) |

(52) U.S. Cl.
CPC ............. *A61L 27/20* (2013.01); *A61L 17/005* (2013.01); *A61L 27/54* (2013.01); *A61L 2430/34* (2013.01)

(58) Field of Classification Search
CPC ..... A61K 31/728; A61L 17/005; A61L 17/10; A61L 2430/34; A61L 27/20; A61L 27/54;
(Continued)

(56) References Cited

U.S. PATENT DOCUMENTS

| | | | |
|---|---|---|---|
| 10,994,048 B2 | 5/2021 | Kweon et al. | |
| 2010/0310631 A1 | 12/2010 | Domard et al. | |

(Continued)

FOREIGN PATENT DOCUMENTS

| | | |
|---|---|---|
| CN | 108350610 A | 7/2018 |
| JP | 2007262595 A | 10/2007 |

(Continued)

*Primary Examiner* — Lynda Salvatore
(74) *Attorney, Agent, or Firm* — NKL Law; Jae Youn Kim

(57) ABSTRACT

A high-strength hyaluronate fiber, suitable for use in a surgical suture, a lifting thread, a tissue-engineering scaffold, etc., and a manufacturing method thereof are proposed. The method includes (a) controlling a water content of a hyaluronate having a weight average molecular weight of 100-3,000 kDa to 50-95 wt % to prepare a hyaluronate paste, (b) melting the hyaluronate paste having a controlled water content at a temperature ranging from room temperature to 100° C., and then extruding the hyaluronate paste through a nozzle, and (c) drying the extruded spinning fluid to form a fiber. The hyaluronate fiber has the water content of 5-25 wt %, the tensile strength of 3 to 15 kg/mm$^2$, and a smooth surface with small cracks, so that the hyaluronate fiber can be used for a surgical suture, a lifting thread, a filler for cosmetic surgery, a tissue-engineering scaffold, etc.

6 Claims, 3 Drawing Sheets

(58) Field of Classification Search
CPC ...... C08B 37/0072; D01D 10/06; D01D 5/08; D01F 9/00
See application file for complete search history.

(56) References Cited

U.S. PATENT DOCUMENTS

2013/0142731 A1    6/2013  Gurtner et al.
2013/0309494 A1   11/2013  Burgert et al.
2018/0243471 A1*   8/2018  Kweon .................... D01D 5/08

FOREIGN PATENT DOCUMENTS

| JP | 2011031034 A | 2/2011 |
| JP | 2014202678 A | 10/2014 |
| JP | 2015-522720 A | 8/2015 |
| JP | 2018527486 A | 9/2018 |
| JP | 2018531123 A | 10/2018 |
| KR | 10-2014-0006851 A | 1/2014 |
| KR | 10-2014-0100469 A | 8/2014 |
| KR | 10-2015-0090167 A | 8/2015 |
| KR | 10-1709608 B1 | 3/2017 |

* cited by examiner

HYALURONATE FIBER AND MANUFACTURING METHOD THEREOF

TECHNICAL FIELD

The present disclosure relates to a hyaluronate fiber and a manufacturing method thereof. More particularly, the present disclosure relates to a high-strength hyaluronate fiber, suitable for use in a surgical suture, a lifting thread, a tissue-engineering scaffold, etc., and a manufacturing method thereof.

BACKGROUND ART

Hyaluronic acid (HA) is a colorless high-viscosity polysaccharide having a molecular weight of 500,000 to 13,000,000 Da, and is configured such that D-glucuronic acid and N-acetylglucosamine, which are repeating units, are alternately linked by (1-3) and (1-4) bonds.

HA is involved in a variety of human physiological activities and is known to have various physiological activities depending on the molecular weight thereof. In particular, polymeric HA is used as a space filler, and is known to possess anti-angiogenic and immunosuppressive functions.

Thus, HA of 2.0 MDa or more in the form of a high-viscosity hydrogel is currently widely utilized as an injecting agent for joints, a filler for cosmetic surgery, and an adhesion inhibitor for internal and external surgery. However, most products are in the form of a liquid such as a high-viscosity aqueous solution or hydrogel, and are thus limited in usability, storability and processability. Moreover, upon use in the form of a liquid, the stability of HA itself decreases, and care should be taken to store and distribute the product. The HA content in the actual product is as low as about 1 to 5%, making it impossible to inject high-concentration HA in a large amount into a human patient, and also, injection pressure due to a high volume thereof leads to great pain for the patient.

Furthermore, when HA is injected in vivo in the form of liquid, it is rapidly degraded by various lyases present in vivo to thus decrease the molecular weight thereof, whereby the persistence in vivo is also lowered and the effect on a treatment site is deteriorated.

With the goal of improving the stability and usability of HA, Korean Patent Application Publication No. 2014-0100469 and Japanese Patent Application Publication No. 2011-31034 disclose a suture in which a safe degradable polymer as a main material is blended or coated with a small amount, specifically 10% or less, of HA, but have problems caused by a low HA content.

In order to solve the problems, Korean Patent No. 10-1709608 discloses a method of manufacturing a hyaluronate fiber through melt spinning, including the steps of: (a) controlling a water content of a hyaluronate having a weight average molecular weight of 500-3,000 kDa to 5-20%; (b) producing a hyaluronate fiber by placing the hyaluronate having a controlled water content in a melt-spinning apparatus, melting the hyaluronate at a temperature ranging from room temperature to 100° C., and then performing high-pressure spinning; and (c) hardening a surface of the hyaluronate fiber by immersing the hyaluronate fiber in an ethanol aqueous solution. However, the hyaluronate fiber manufactured by the method of Korean Patent No. 10-1709608 has a high content of hyaluronate, but is problematic in that high pressure is required during spinning, so that it is difficult to mass produce the hyaluronate fiber and the surface of the produced fiber is rough.

Therefore, the present inventors have made efforts to solve the above problems and thus have ascertained that, when a hyaluronate paste having the water content of 50-95 wt % is made, melted, extruded through a nozzle, and then dried, it is possible to mass produce a hyaluronate fiber having a smooth surface and a high tensile strength, thus culminating in the present disclosure.

DISCLOSURE

Technical Problem

Therefore, an objective of the present disclosure is to provide a high-strength hyaluronate fiber which contains a high concentration of hyaluronate and has a uniform surface, and a manufacturing method thereof.

Another objective of the present disclosure is to provide a surgical suture, a filler for cosmetic surgery, a lifting thread, and a tissue-engineering scaffold, manufactured using the hyaluronate fiber having high safety and biocompatibility.

Technical Solution

In order to accomplish the above objectives, the present disclosure provides a hyaluronate fiber having a bending angle of 2 to 10° when measured by the following method of measuring the binding angle, a water content of 5 to 25 wt %, and a hyaluronate content of 90 wt % or more, based on a total fiber weight excluding water:

<Method of Measuring the Bending Angle>
- (a) preparing HA fiber having a length of 20 cm and a diameter of 1 mm,
- (b) fixing 3 cm of a first end of the HA fiber to an upper surface of a flat plate, and
- (c) measuring an angle ($\theta$) between an upper-surface extension line (B) of the flat plate and an extension line (T) of a second end of the HA fiber.

The hyaluronate fiber may have a tensile strength of 3 to 15 $kg/mm^2$.

A crack amount of the hyaluronate fiber may be 15% or less of a surface area of the fiber.

The present disclosure provides a method of manufacturing a hyaluronate fiber, including (a) controlling a water content of a hyaluronate having a weight average molecular weight of 100-3,000 kDa to 50-95 wt % to prepare a hyaluronate paste;
  (b) melting the hyaluronate paste having a controlled water content at a temperature ranging from room temperature to 100° C., and then extruding the hyaluronate paste through a nozzle; and (c) drying the extruded spinning fluid to form a fiber.

The drying may be performed at a temperature ranging from room temperature to 100° C.

The present disclosure provides a surgical suture, including the hyaluronate fiber.

The present disclosure provides a filler for cosmetic surgery, including the hyaluronate fiber.

The present disclosure provides a lifting thread, including the hyaluronate fiber.

The present disclosure provides a tissue-engineering scaffold, including the hyaluronate fiber.

Advantageous Effects

According to the present disclosure, a hyaluronate fiber has the water content of 5-25 wt % and has a smooth surface with small cracks, so that the hyaluronate fiber can be used for a surgical suture, a lifting thread, a filler for cosmetic surgery, a tissue-engineering scaffold, etc.

BEST MODE

According to the present disclosure, when a hyaluronate paste having a water content that is controlled to be in a predetermined range is melted, extruded through a nozzle, and then dried, it is possible to manufacture a hyaluronate fiber having a high strength and a smooth surface without cracks.

In the present disclosure, the hyaluronate fiber is manufactured through the following method. First, the hyaluronate paste is prepared by controlling the percentage of water content of a hyaluronate to 50-95 wt %. The hyaluronate paste is melted at a temperature ranging from room temperature to 100° C., and then is extruded through the nozzle. Subsequently, this is dried at a temperature ranging from room temperature to 100° C., thus manufacturing the hyaluronate fiber.

As a result, it is possible to mass produce a hyaluronate fiber in which a water content thereof ranges from 5 to 25 wt %, a tensile strength thereof ranges from 3 to 15 kg/md, and a surface thereof is smooth without cracks.

Therefore, the present disclosure is directed to a hyaluronate fiber having a bending angle of 2 to 10° when measured by the following measuring method, a water content of 5 to 25 wt %, and a hyaluronate content of 90 wt % or more, based on a total fiber weight excluding water.

Figure 1:
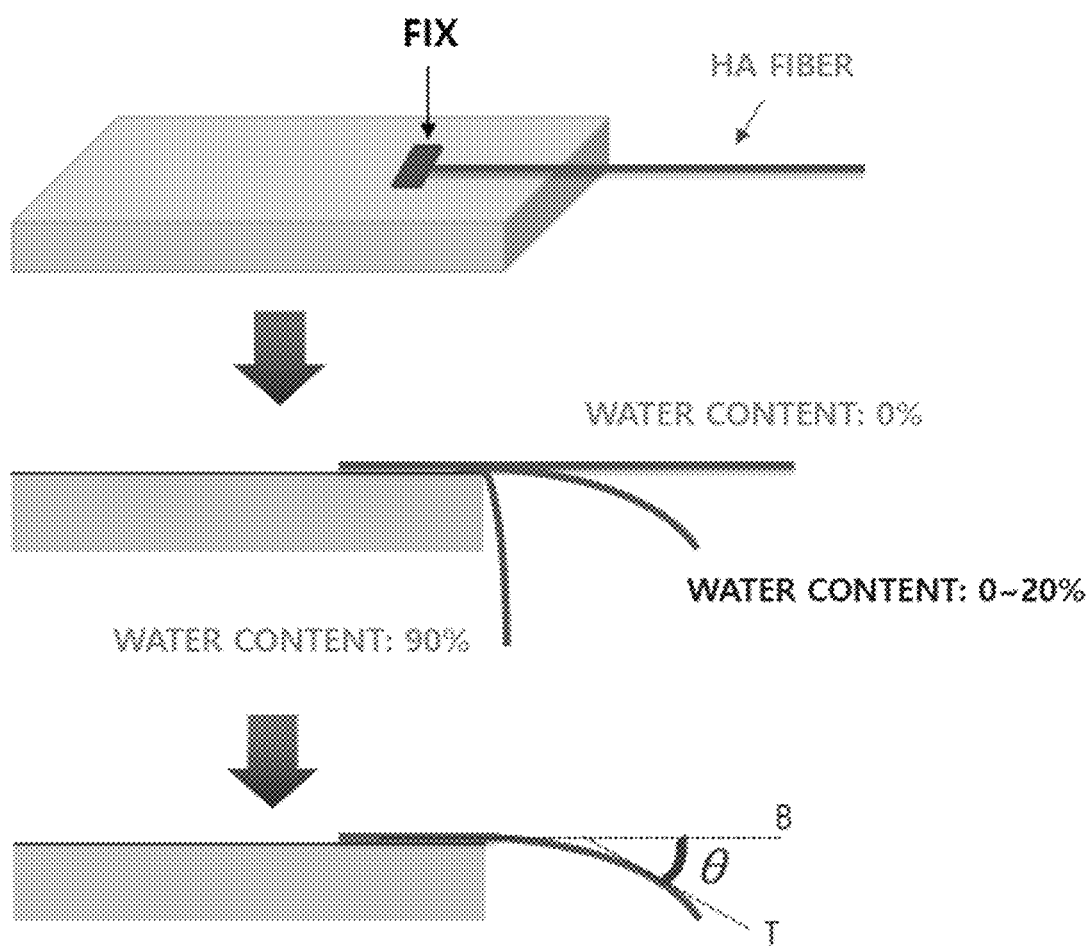
FIG. 1 illustrates a process of measuring a bending angle of a hyaluronate fiber in accordance with an embodiment of the present disclosure.

As shown in FIG. 1, the method of measuring the bending angle of the hyaluronate fiber is as follows:
  (a) preparing HA fiber having a length of 20 cm and a diameter of 1 mm,
  (b) fixing 3 cm of one end of the HA fiber to an upper surface of a flat plate, and
  (c) measuring an angle θ between an upper-surface extension line B of the flat plate and an extension line (T) of the other end of the HA fiber.

In the present disclosure, the bending angle of the hyaluronate fiber relates to the convenient use of the hyaluronate fiber during a surgical procedure, and preferably ranges from 2 to 10°. When the bending angle is less than 2° and more than 10°, the convenience of using the fiber is reduced.

In the present disclosure, the water content of the hyaluronate fiber affects the bending angle, microbial contamination, and physical properties, and preferably ranges from 5 to 25 wt %, more preferably 5 to 15 wt %. When the water content is less than 5 wt %, the fiber maintains its shape but is hardened and inflexible, so that the fiber is easily broken. On the other hand, when the water content is more than 25 wt %, the fiber does not maintain its shape or does not properly perform its function.

Since the hyaluronate fiber of the present disclosure may be made exclusively of hyaluronate, the fiber has the hyaluronate content of 90-100 wt %, based on a total fiber weight excluding water. Depending on an application field, carriers or excipients which are commonly used in the art may be additionally included, but their types and content ranges are not particularly limited.

The hyaluronate fiber of the present disclosure has the tensile strength of 3 to 15 kg/md, and the crack amount of the fiber is 15% or less of the surface area of the fiber. In the present disclosure, the crack amount indicates the smoothness of the surface of the hyaluronate fiber. The crack amount may be measured by capturing the image of the surface of the hyaluronate fiber with a microscope and then calculating a ratio of cracks, such as pores (grooves) or linear gaps, present in a total hyaluronic-fiber image capturing area. The crack amount is preferably 15% or less. Meanwhile, when the crack amount exceeds 15%, this is not preferable because there is a risk of causing damage to the skin during the procedure.

Further, the present disclosure is directed to a method of manufacturing a hyaluronate fiber, including the steps of: (a) controlling a water content of a hyaluronate having a weight average molecular weight of 100-3,000 kDa to 50-95 wt % to prepare a hyaluronate paste; (b) melting the hyaluronate paste having a controlled water content at a temperature ranging from room temperature to 100° C., and then extruding the hyaluronate paste through a nozzle; and (c) drying the extruded spinning fluid to form a fiber.

In the present disclosure, the hyaluronate is produced by linking salt to hyaluronic acid. Examples of the hyaluronate may include sodium hyaluronate, calcium hyaluronate, and potassium hyaluronate, but the present disclosure is not limited thereto.

In the present disclosure, the hyaluronate preferably has the molecular weight of 100 to 3,000 kDa. Further, the water content in the hyaluronate of the hyaluronate paste ranges from 50 to 95 wt %.

The hyaluronate paste may be prepared by adding solvent to the hyaluronate. The solvent may use water or ethanol aqueous solution. It is preferable to perform a mixing operation until the solvent is uniformly mixed.

In order to smoothly perform the mass spinning process, the water content of the hyaluronate paste may range from 50 to 95 wt %, and preferably 88 to 92 wt %. When the water content is less than 50 wt %, high pressure is required during the spinning operation, and a large amount of cracks may be present in the manufactured fiber. On the other hand, when the water content is more than 95 wt %, the hyaluronate paste is in the form of liquid rather than paste, so that the fiber may be undesirably broken during the spinning operation.

In the present disclosure, after the hyaluronate paste is prepared, it is left at 0 to 100° C. for 6 to 12 hours to attain water equilibrium. When the temperature and the time are out of the above-described ranges, the water equilibrium is not properly achieved. The water equilibrium enables water molecules of the paste and the hyaluronic acid to be evenly mixed with each other. In the case of performing the spinning operation without the water equilibrium, the water molecules and the hyaluronic acid are not evenly mixed with each other, so that it is impossible to perform the spinning operation at a constant rate, or the crack amount in the manufactured fiber may be undesirably increased.

In the present disclosure, the hyaluronate paste having the water content controlled to 50-95 wt % is put into a spinning apparatus, is melted at a temperature ranging from room temperature to 100° C., and then is extruded through the nozzle, thus preparing spinning fluid. Here, when the temperature is less than about 15° C. that is room temperature, the hyaluronate paste is not melted and thereby is not extruded. On the other hand, when the temperature is more than 100° C., the paste may be undesirably boiled.

In the present disclosure, the extruded spinning fluid is dried, thus finally producing fiber. The drying operation is preferably performed at a temperature ranging from room temperature to 100° C. depending on the water content of the paste.

Since the hyaluronate fiber manufactured according to the present disclosure may have a hyaluronate content of 90 wt % or more, have a water content of 5 to 25 wt %, have a tensile strength of 3 to 15 kg/md, and have a smooth surface, there is no microbial contamination and it is easy to manage and use, so that the hyaluronate fiber of the present disclosure can be efficiently used in various types of tissue repair products, unlike an existing liquid hyaluronate tissue repair product.

Thus, the present disclosure addresses a surgical suture, a filler for cosmetic surgery, a lifting thread, and a tissue-engineering scaffold including the aforementioned hyaluronate fiber.

Mode for Invention

A better understanding of the present disclosure may be obtained through the following examples, which are set forth to illustrate, but are not to be construed as limiting the scope of the present disclosure, as will be apparent to those skilled in the art.

Example 1

Preparation of Hyaluronate Paste

Water was applied to sodium hyaluronate (Hi-Aqua™, made by JinWOO Bio) having a molecular weight of 150 kDa, and then was mixed and kneaded to prepare a hyaluronate paste having a water content of 50-95 wt %.

The prepared hyaluronate paste was cold-stored at 4° C. for 12 hours to create water equilibrium.

Example 2

Production of Hyaluronate Fiber by Spinning

The hyaluronate paste prepared in Example 1 was placed in a storage section of a spinning apparatus, melted at a temperature ranging from room temperature to 100° C., pressurized, and spun through a nozzle, followed by drying at 40° C., thus manufacturing a hyaluronate fiber having a water content of 0-95 wt %.

Comparative Example 1

Preparation of Hyaluronate Paste

Water was applied to sodium hyaluronate (Hi-Aqua™, made by JinWOO Bio) having a molecular weight of 150 kDa, and then was mixed and kneaded to prepare a hyaluronate paste having a water content of 5-40 wt %. The prepared hyaluronate paste was cold-stored at 4° C. for 12 hours to create water equilibrium.

Comparative Example 2

Preparation of Hyaluronate Paste

Water was applied to sodium hyaluronate (Hi-Aqua™, made by JinWOO Bio) having a molecular weight of 150 kDa, and then was mixed and kneaded to prepare a hyaluronate paste having a water content of 85 wt %. Water equilibrium was not created.

Comparative Example 3

Production of Hyaluronate Fiber by Spinning

The hyaluronate paste prepared in Comparative Example 1 was placed in a storage section of a spinning apparatus, melted at a temperature ranging from room temperature to 100° C., pressurized, and spun through a nozzle, followed by drying at 40° C., thus manufacturing a hyaluronate fiber having a water content of 0-95 wt %.

Comparative Example 4

Production of Hyaluronate Fiber by Spinning

The hyaluronate paste prepared in Comparative Example 2 was placed in a storage section of a spinning apparatus, melted at a temperature ranging from room temperature to 100° C., pressurized, and spun through a nozzle, followed by drying at 40° C., thus manufacturing a hyaluronate fiber having a water content of 0-95 wt %.

Test Example 1

Spinning-Process Evaluation Depending on Water Content of Hyaluronate Paste

The hyaluronate paste prepared in each of Example 1 and Comparative Example 1 was placed in a storage section of a spinning apparatus, melted at a temperature ranging from room temperature to 100° C., pressurized, and spun through a nozzle, followed by drying at 40° C., thus manufacturing a hyaluronate fiber having a water content of 0-95 wt %. A spinning speed was evaluated.

Consequently, Example 1 where the water content of the hyaluronate paste is 50-95 wt % showed a spinning speed of 0.05 m/min, and Comparative Example 1 where the water content is 5-40 wt % showed a spinning speed of 0.4 m/min.

Test Example 2

Bending-Angle Measurement of Hyaluronate Fiber

The bending angle of the hyaluronate fiber manufactured in Example 2 was measured by the following method, and the measured results are shown in Table 1.

(a) Preparing HA fiber having the length of 20 cm and the diameter of 1 mm.

(b) Fixing 3 cm of one end of the HA fiber to an upper surface of a flat plate.

(c) Measuring an angle $\theta$ between an upper-surface extension line B of the flat plate and an extension line T of the other end of the HA fiber.

TABLE 1

| Percentage of Water Content in Hyaluronate Fiber (wt %) | Bending Angle (°) |
| --- | --- |
| 95 | 90 |
| 50 | 80 |
| 25 | 10 |
| 20 | 8 |
| 10 | 3 |

TABLE 1-continued

| Percentage of Water Content in Hyaluronate Fiber (wt %) | Bending Angle (°) |
|---|---|
| 5 | 2 |
| 0 | 0 |

From Table 1 above, when the water content in the hyaluronate fiber is 50 wt % or more, the bending angle was 80° or more. Thus, it is determined that this does not support cells and does not maintain its shape when injected into the human body, so that the fiber will not properly perform its function.

Furthermore, when the percentage of water content in the hyaluronate fiber is less than 5 wt %, it can be seen that the fiber maintains its shape but is hardened and inflexible, so that the fiber is easily broken.

In contrast, when the percentage of water content in the hyaluronate fiber ranges from 5 to 25 wt %, it can be seen that the bending angle is 2 to 10°, so that this is a suitable type of hyaluronate fiber during a procedure.

Test Example 3

Tensile-Strength Measurement of Hyaluronate Fiber

The tensile strength of the hyaluronate fiber manufactured in Example 2 was measured, and the measured results are shown in Table 2. The tensile strength was measured using a universal testing machine with a sample having the length of 5 cm being mounted on a test jig and a crosshead speed being set to 2 mm/min.

TABLE 2

| Percentage of Water Content In Hyaluronate Fiber (wt %) | Tensile Strength (kg/mm$^2$) |
|---|---|
| 95 | Not Measurable |
| 50 | 0.27 |
| 30 | 2.83 |
| 25 | 3.24 |
| 20 | 5.29 |
| 10 | 10.53 |
| 5 | 13.38 |
| 0 | Not Measurable |

From Table 2 above, when the water content in the hyaluronate fiber is 50 wt % or more, it is determined that the tensile strength is rapidly reduced, is easily broken, and has no elasticity, so that the fiber cannot properly perform its function.

Furthermore, when the percentage of water content in the hyaluronate fiber is 5 wt % or less, the fiber maintains its shape but is hardened and easily broken, so that the tensile strength cannot be measured.

In contrast, when the percentage of water content in the hyaluronate fiber ranges from 5 to 25 wt %, it can be seen that the tensile strength ranges from 3.24 to 13.38 kg/mm$^2$, and thereby this is the hyaluronate fiber that has the shape and function of a thread.

Test Example 4

Check of Crack Amount of Hyaluronate Fiber

An image of a surface of the hyaluronate fiber manufactured in each of Example 2 and Comparative Examples 3 and 4 was captured by a microscope (magnification: 200×). After the image of the surface of the hyaluronate fiber was captured through the microscope, an image was processed by the image processing software "Photoshop" (Adobe Systems Inc.), an image analysis software "Scion Image" (Scion Corporation) was used, and a crack amount was quantified. The results are shown in Table 3 and FIGS. 2 to 4.

TABLE 3

| | Hyaluronate fiber | Crack Amount | Note |
|---|---|---|---|
| A | Example 2: Water Content in Hyaluronate Fiber 10 wt % | 3-10% | — |
| B | Example 2: Water Content in Hyaluronate Fiber 20 wt % | 2-7% | FIG. 2 |
| C | Example 2: Water Content in Hyaluronate Fiber 50 wt % | 1-5% | — |
| D | Comparative Example 3: Water Content in Hyaluronate Fiber 10 wt % | 20-30% | FIG. 3 |
| E | Comparative Example 4: Water Content in Hyaluronate Fiber 10 wt % | 25-35% | FIG. 4 |

Figure 2:
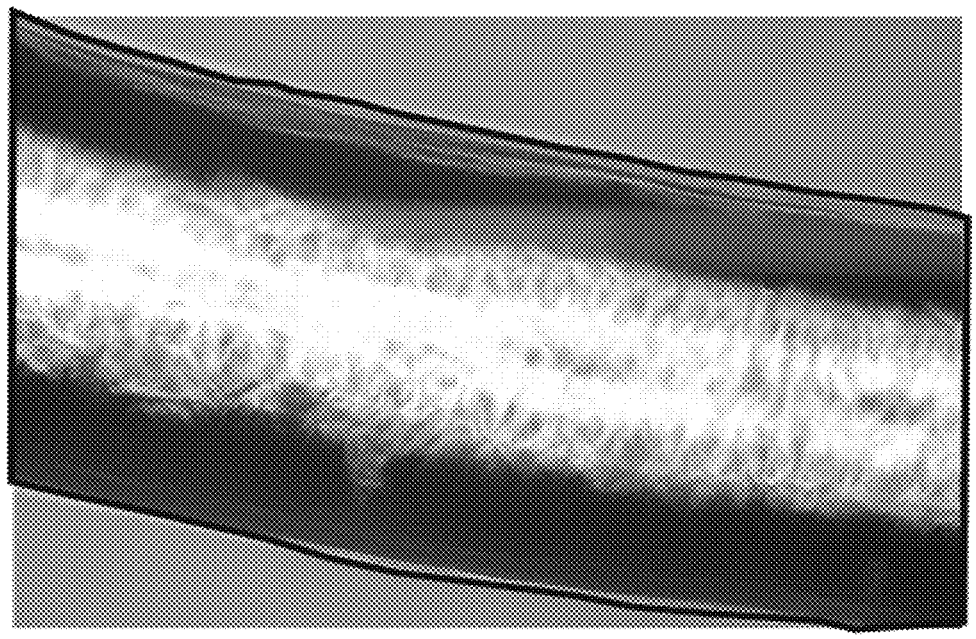
FIGS. 2 to 4 are micrographs of the surface of the hyaluronate fiber manufactured by the present disclosure.
Figure 3:
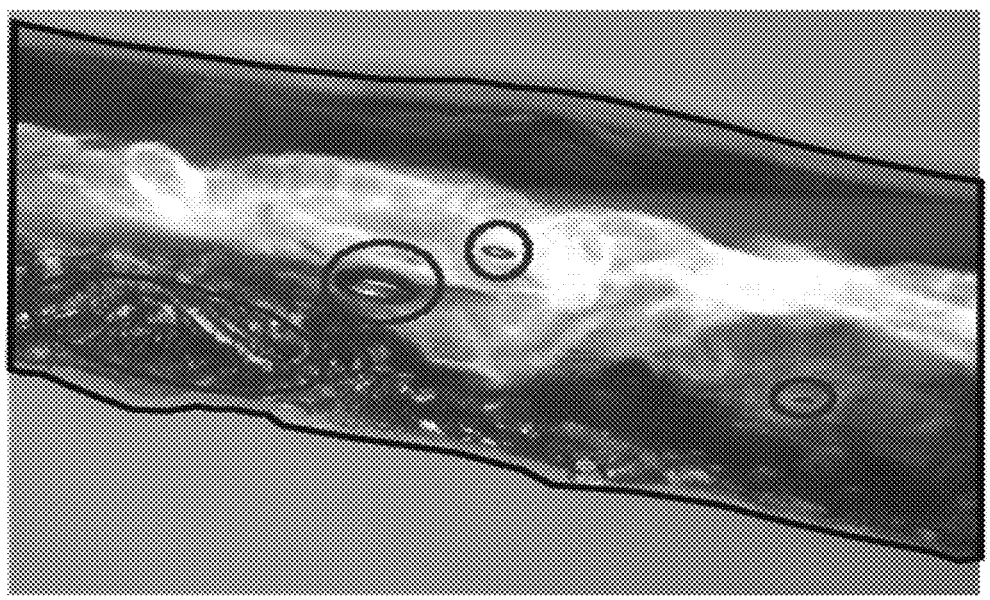
Figure 4:
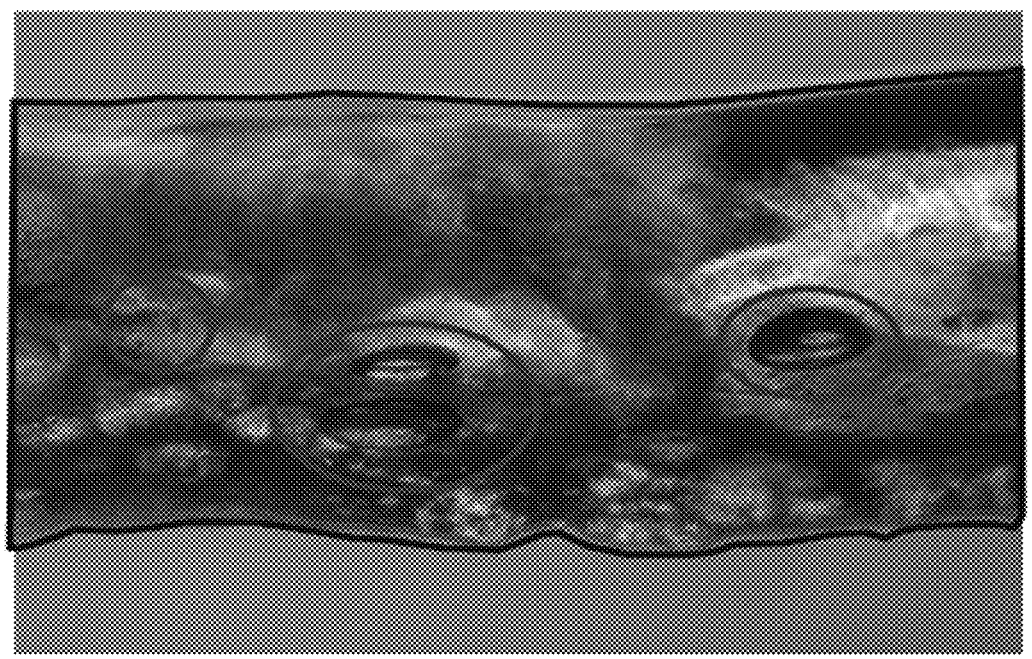

From Table 3 above and FIGS. 2 to 4, in the case of A, B, and C in which the water content of the hyaluronate paste ranges from 50 to 95 wt % and which is manufactured through the water equilibrium, it can be seen that the crack amount is reduced in reverse proportion to the water content of the finished hyaluronate fiber.

In contrast, in the case of both D which is manufactured through the water equilibrium using the hyaluronate paste having the water content of 5 to 40 wt %, and E which is manufactured without the water equilibrium, it can be seen that the crack amount is increased.

For reference, in FIGS. 2 to 4, a total hyaluronic-fiber image capturing area was indicated by a blue line (rectangle), and cracks such as pores (grooves) or linear gaps were indicated by a red line (circle).

Although specific embodiments of the present disclosure have been disclosed in detail as described above, it is obvious to those skilled in the art that such description is merely of preferable exemplary embodiments and is not construed to limit the scope of the present disclosure. Therefore, the substantial scope of the present disclosure will be defined by the appended claims and equivalents thereof.

INDUSTRIAL APPLICABILITY

Since the hyaluronate fiber of the present disclosure has a smooth surface with a small crack, the hyaluronate fiber can be used for a surgical suture, a lifting thread, a filler for cosmetic surgery, a tissue-engineering scaffold, etc.

The invention claimed is:

1. A hyaluronate fiber having a water content of 5 to 25 wt %, a crack amount of 15% or less of a surface area of the hyaluronate fiber, and a hyaluronate content of 90 wt % or more, based on a total fiber weight excluding water.

2. The hyaluronate fiber of claim 1, wherein the hyaluronate fiber has a tensile strength of 3 to 15 kg/mm$^2$.

3. A surgical suture, comprising the hyaluronate fiber of claim 1.

4. A filler for cosmetic surgery, comprising the hyaluronate fiber of claim 1.

5. A lifting thread, comprising the hyaluronate fiber of claim 1.

6. A tissue-engineering scaffold, comprising the hyaluronate fiber of claim 1.

* * * * *